(12) United States Patent
Goto

(10) Patent No.: US 6,411,906 B1
(45) Date of Patent: Jun. 25, 2002

(54) METHOD AND SYSTEM FOR INSPECTING POLYCRYSTALLINE SEMICONDUCTOR FILM

(75) Inventor: Yasumasa Goto, Fukaya (JP)

(73) Assignee: Kabushiki Kaisha Toshiba, Kanagawa-ken (JP)

( * ) Notice: Subject to any disclaimer, the term of this patent is extended or adjusted under 35 U.S.C. 154(b) by 0 days.

(21) Appl. No.: 09/245,312

(22) Filed: Feb. 5, 1999

(30) Foreign Application Priority Data

Feb. 6, 1998 (JP) .......................................... 10-026115

(51) Int. Cl.$^7$ ............................................. H01L 21/31
(52) U.S. Cl. ...................... 702/28; 438/486; 438/488; 700/123
(58) Field of Search ................................ 438/166, 486, 438/488; 702/28, 170; 356/369; 700/121, 123; 257/64

(56) References Cited

U.S. PATENT DOCUMENTS

| | | | | |
|---|---|---|---|---|
| 5,314,831 A | * | 5/1994 | Hirae et al. ..................... 437/8 |
| 6,128,084 A | * | 10/2000 | Nanbu et al. ................ 356/369 |
| 6,218,313 B1 | * | 4/2001 | Tomita et al. ............... 438/758 |
| 6,233,046 B1 | * | 5/2001 | Alba et al. ..................... 356/38 |

FOREIGN PATENT DOCUMENTS

JP    4-43661    2/1992

OTHER PUBLICATIONS

Robinson et al., "Correlation of Ellipsonometric Modeling Results To Observed Grain Structure for OPO Film Stacks", IEEE, 1998.*

* cited by examiner

Primary Examiner—Patrick Assouad
(74) Attorney, Agent, or Firm—Pillsbury Winthrop LLP

(57) ABSTRACT

Standard samples including at least a polycrystalline semiconductor film are produced by the energy beam annealing method. Dependencies on wavelength of refractive index and damping coefficients of standard samples are measured by means of a spectral ellipsometer, and grain sizes are measured to be quantified. An estimated sample consisting of a polycrystalline semiconductor film is produced by means of the energy beam annealing method. A dependency on wavelength of a refractive index and a damping coefficient of the estimated sample is measured to be compared with the results of the standard sample. Thus, the optically measured results can be quantified, so that it is possible to accurately measure a mean grain size of a polycrystalline silicon of a sample to be estimated, in a short time of about 5 seconds to calculate mobility to accurately select non-defective from defective in a short time.

16 Claims, 13 Drawing Sheets

METHOD AND SYSTEM FOR INSPECTING POLYCRYSTALLINE SEMICONDUCTOR FILM

BACKGROUND OF THE INVENTION

The present invention relates generally to a method and system for inspecting a polycrystalline semiconductor film. More specifically, the invention relates to an inspecting method and system for measuring grain sizes of semiconductor grains forming a polycrystalline semiconductor film.

In general, a thin film transistor (TFT) using a polycrystalline silicon (poly-Si) has an advantage in that the crystal has a mobility 10 through 100 times as high as that of a TFT using an amorphous silicon (a-Si). Therefore, there has been studied and developed a drive circuit integrated thin film transistor-liquid crystal display (TFT-LCD) wherein a thin film transistor of a polycrystalline silicon is not only used as a pixel switching element for the liquid crystal display (LCD), but it is also used as a peripheral drive circuit for the liquid crystal display, to form the thin film transistors for the pixel and the drive circuit on the same substrate. In such a drive circuit integrated TFT-LCD, there is a correlation that the mobility of crystals of a thin film transistor of a polycrystalline silicon increases as the crystal grain size increases, as can be seen from a characteristic diagram of FIG. 1 which shows the relationship between the crystal grain size and mobility. For that reason, there is an important problem of how to measure the crystal grain size.

Conventionally, the crystal grain size is measured by a scanning electron beam microscope (SEM) or the like after a grain boundary is selectively removed by an etching, such as SECO etching, or a cross section taken along a thickness direction of a substrate is observed by a transmission electron beam microscope (TEM). However, in such conventional inspection methods, it takes at least 2 hours to observe the grain size. In order to shorten the measuring time, it has been proposed to use an atomic beam frequency microscope (AFM). Although the grain size can be observed and measured by the AFM, it takes about 30 minutes to observe a one point to analyze the grain size.

In addition, there is well known a basic method for observing a grain size by means of an optical microscope having a magnification of 500 thorough 1000 by using the variation in irregularity on the surface of a film as an index of the grain size. However, since this method is greatly relied on the human naked eye, the measured results are easily influenced by the difference among individuals, so that there are problems in that quite accurate results can not be obtained and the measured results are not quantitative.

Moreover, there may be considered a grain size analysis using an ellipsometer which can measure a grain size in a non-destructive and non-contact manner in a short measuring time of 5 seconds per one point This conventional measuring method using the ellipsometer is used for analyzing an object having a flat surface, such as a silicon oxide film on a single crystal. However, if this method is used for analyzing a polycrystalline silicon, there is a problem in that it is difficult to construct an analysis model, e.g., it is difficult to quantify the grain size, mobility and so forth. Particularly in the case of the conventional ellipsometer measuring method, a polycrystalline silicon produced by the excimer laser annealing (ELA) method has irregularities on the surface even if the thickness thereof is, e.g., about 50 nm, so that it is particularly difficult to quantify the grain size, mobility and so forth. On the other hand, in a polycrystalline semiconductor film inspecting method according to the present invention, a polycrystalline semiconductor film having surface irregularities produced by the ELA is used as a sample, and a polycrystalline semiconductor film is also used as a reference sample.

For example, when 12-inch and 15-inch or more drive circuit integrated thin film transistor-liquid crystal displays are produced, the mean grain sizes of the polycrystalline silicon are suitably 0.25 $\mu$m and 0.45 $\mu$m or more, respectively. Because, in the case of a display size of 12 inches, the mobility of crystals in n-channel lightly doped drain-thin film transistors (n-ch LDD-TFT) having a grain size of 0.25 $\mu$m or less is 100 cm$^2$/Vs or less, so that it is difficult to drive a 12-inch class LCD. In addition, because, in the case of a display size of 15 inches, the mobility of crystals in n-channel lightly doped drain-thin film transistors (n-ch LDD-TFT) having a grain size of 0.45 $\mu$m or less is 120 cm$^2$/Vs or less, so that it is difficult to drive a 15-inch class or more LCD. Therefore, the polycrystalline silicon films of the drive circuit integrated thin film transistor-liquid crystal displays are preferably prepared so as to have grain sizes of about 0.25 $\mu$m and about 0.45 $\mu$m, respectively. However, it is impossible to accurately measure the polycrystalline silicon films having this range of grain size in a short time.

In conventional methods, e.g., in a method utilizing the relationship between mean grain sizes of a polycrystalline silicon and proportions of compositions of the polycrystalline silicon when the polycrystalline silicon is represented as a mixture of an amorphous silicon and a crystalline silicon (c-Si), as shown in FIG. 2, or in a method utilizing the relationship between mean grain sizes of a polycrystalline silicon and proportions of compositions of the polycrystalline silicon when the polycrystalline silicon is represented as a mixture of an amorphous silicon, a polycrystalline silicon and a crystalline silicon, as shown in FIG. 3, there is a problem in that there is no repeatability in a sample having a thickness difference of ±5%, so that it is not possible to achieve accuracy which can be utilzed in the measurement of grain sizes. Because both of the thickness and quality of a film are simultaneously calculated as parameters during analysis. That is, if only the thickness of the film is determined before the calculation of the quality of the film, the quality of the film is different from that of an actual sample. Moreover, if the quality of the film is calculated using the determined thickness of the film, it is required to calculate the thickness again using the calculated quality of the film.

In addition, the surface of polycrystalline silicon is coated with a natural oxide film, and a polycrystalline silicon film formed by the ELA method has surface irregularities as an inherent property, so that there is a problem in that conventional analyzing methods for use in polycrystalline silicon film having a flat surface can not be used. An example of such conventional polycrystalline silicon inspecting methods is disclosed in 1992 American Institute of Physics, J. Appl. Phys. 72(8), Oct. 15, 1992, "Comparative study of thin poly-Si films grown by ion implantation and annealing with spectroscopic ellipsometry, raman spectroscopy, and electron microscopy". It is reported in this literature that the peak width at half height obtained by differentiating, two times, the peak near 4 eV appeared with a dielectric constant ($\in$) of a polycrystalline silicon is used as a parameter.

However, according to the above described conventional inspecting method, there is a problem in that the grain size of a polycrystalline silicon of 0.8 $\mu$m is estimated as 0.05 $\mu$m. In addition, an object to be estimated must have a grain size of 0.15 $\mu$m or less, and this has a low mobility, so that there is a problem in that this can not be used for forming a TFT channel for a liquid crystal display.

As described above, in any conventional inspection methods, it is difficult to quantify the grain size, mobility and so forth of crystals in analysis of the grain size, and it is difficult to accurately measure the crystal grain size in a short time.

SUMMARY OF THE INVENTION

It is therefore an object of the present invention to eliminate the aforementioned problems and to provide a method and system for inspecting a polycrystalline semiconductor film, which can accurately measure the grain size of the polycrystalline semiconductor film in a short time in a non-destructive and non-contact manner.

In order to accomplish the aforementioned and other objects, according to one aspect of the present invention, a polycrystalline semiconductor film inspecting method comprises the steps of: calculating dependencies on wavelength of refractive index and damping coefficients of a plurality of standard samples including at least a polycrystalline semiconductor film; calculating dependency on wavelength of a refractive index and a damping coefficient, and a thickness, of an estimated sample consisting of a polycrystalline semiconductor film; comparing the dependencies on wavelength of the refractive index and the damping coefficient of the estimated sample, with those of the standard samples so as to derive the compared results as indexes; and deriving a correlation between the thickness of the estimated sample and indexes derived as the comparison results. Thus, the standard sample and the sample to be estimated, which serves as the object to be inspected, are measured, so that it is possible to quantify the optically measured results and it is possible to accurately measure a crystal grain size in a short time even in a non-destructive and non-contact manner.

The dependencies on wavelength of the refractive index and the damping coefficient of the polycrystalline semiconductor film serving as the object to be estimated may be compared with those of at least one of an amorphous semiconductor and a crystalline semiconductor. Thus, it is possible to more accurately measure the grain size.

In addition, a correlation between the thickness of the polycrystalline semiconductor film and the indexes serving as the comparison results may be derived, and the polycrystalline semiconductor film serving as the object to be estimated may be annealed while adjusting energy in accordance with the correlation. Thus, the polycrystalline semiconductor film can have a desired grain size.

Moreover, $\Psi$ and $\Delta$, which represent a ratio of a reflectance of a p-polarized light to that of an s-polarized light by $\tan(\Psi) \cdot \exp(i\Delta)$, may be substituted for the dependencies on wavelength of the refractive index and the damping coefficient.

According to another aspect of the present invention, a polycrystalline semiconductor film inspecting method comprises the steps of: irradiating a polycrystalline semiconductor film, which is formed on a substrate, with a light, and detecting dependence on wavelength of the intensity of a reflected light; and comparing the dependence on wavelength of the intensity of the reflected light with a sample data, and calculating a crystal grain size of the polycrystalline semiconductor film or data correlate therewith.

Furthermore, the functional formulae for deriving dependencies on wavelength should not be limited to specific formulae, but any functional formulae may be used as long as the formulae meet a predetermined correlation. That is, the feature of the present invention is that data are previously derived on the basis of the measured results of a plurality of standard samples, and the same data on a sample to be estimated are measured to derive the inspected results, or a polycrystalline semiconductor film meeting desired conditions is derived by processing the derived results while being compared with the results of the standard samples.

DESCRIPTION OF THE PREFERRED EMBODIMENTS

Referring now to the accompanying drawings, the preferred embodiments of a method and system for inspecting a polycrystalline semiconductor film according to the present invention will be described in detail below. First, the concept of a polycrystalline semiconductor used in the specification will be described. In semiconductors for use in TFT-LCDs or the like, it is well known that impurities, such as boron (B), phosphorus (P) and arsenic (As), are implanted into the semiconductors in order to adjust the threshold voltage Vth of TFTs. Therefore, throughout the specification, the semiconductor films for use in the present invention include thin films formed by implanting impurities, such as boron (B), phosphorus (P) and arsenic (As), into semiconductors, such as silicon (Si), germanium (Ge), gallium arsenide (GaAs) and cadmium selenide (CdSe).

Figure 1:
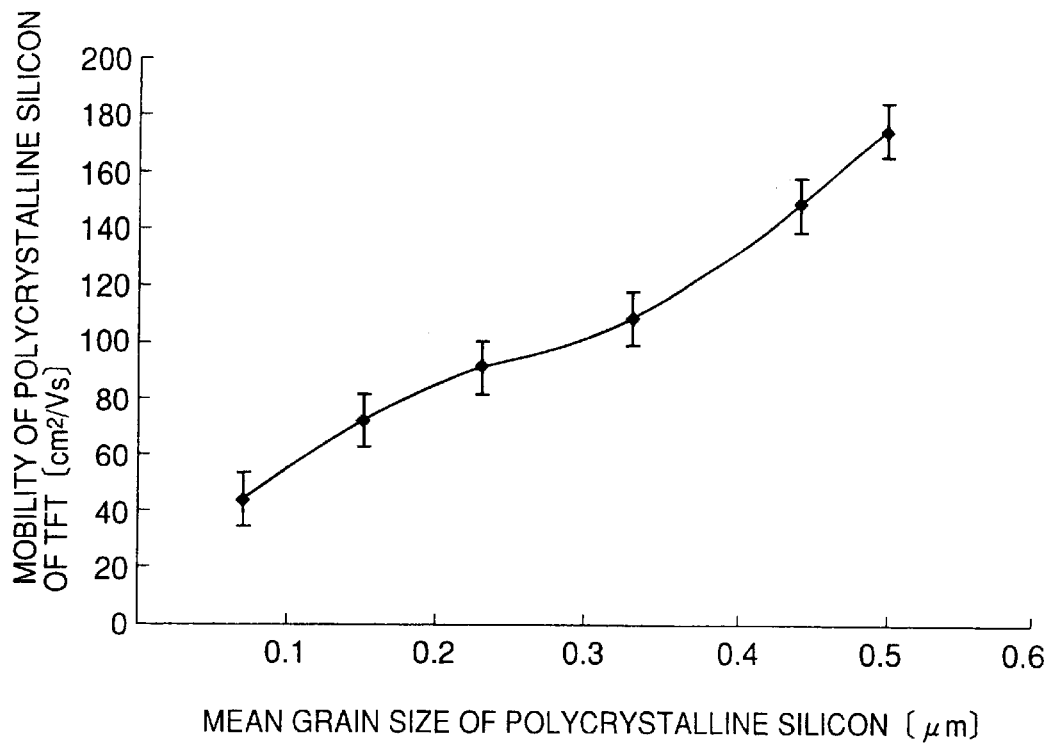
FIG. 1 is a graph showing the relationship between mobility of a thin film transistor of a polycrystalline silicon and mean grain sizes of the polycrystalline silicon.
Figure 2:
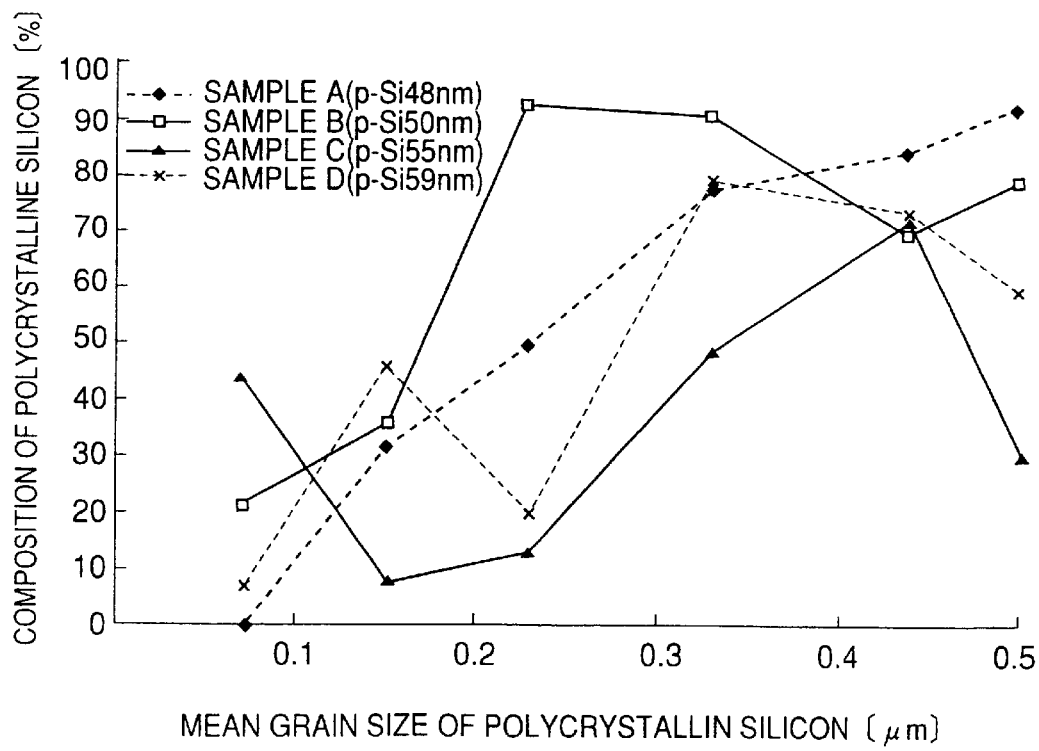
FIG. 2 is a graph showing the relationship between mean grain sizes of a polycrystalline silicon and proportions of compositions of the polycrystalline silicon when the polycrystalline silicon is represented as a mixture of an amorphous silicon and a crystalline silicon.
Figure 3:
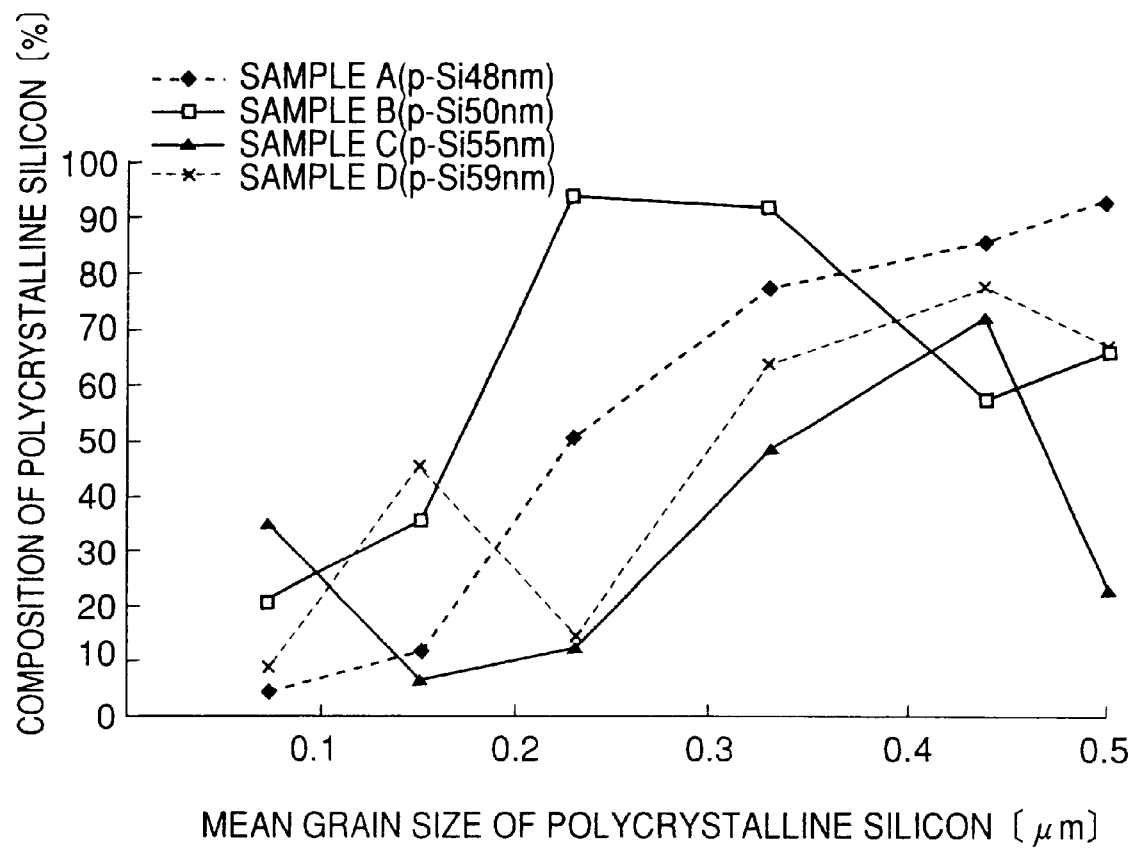
FIG. 3 is a graph showing the relationship between mean grain sizes of a polycrystalline silicon and proportions of compositions of the polycrystalline silicon when the polycrystalline silicon is represented as a mixture of an amorphous silicon, a polycrystalline silicon and a crystalline silicon.
Figure 4:
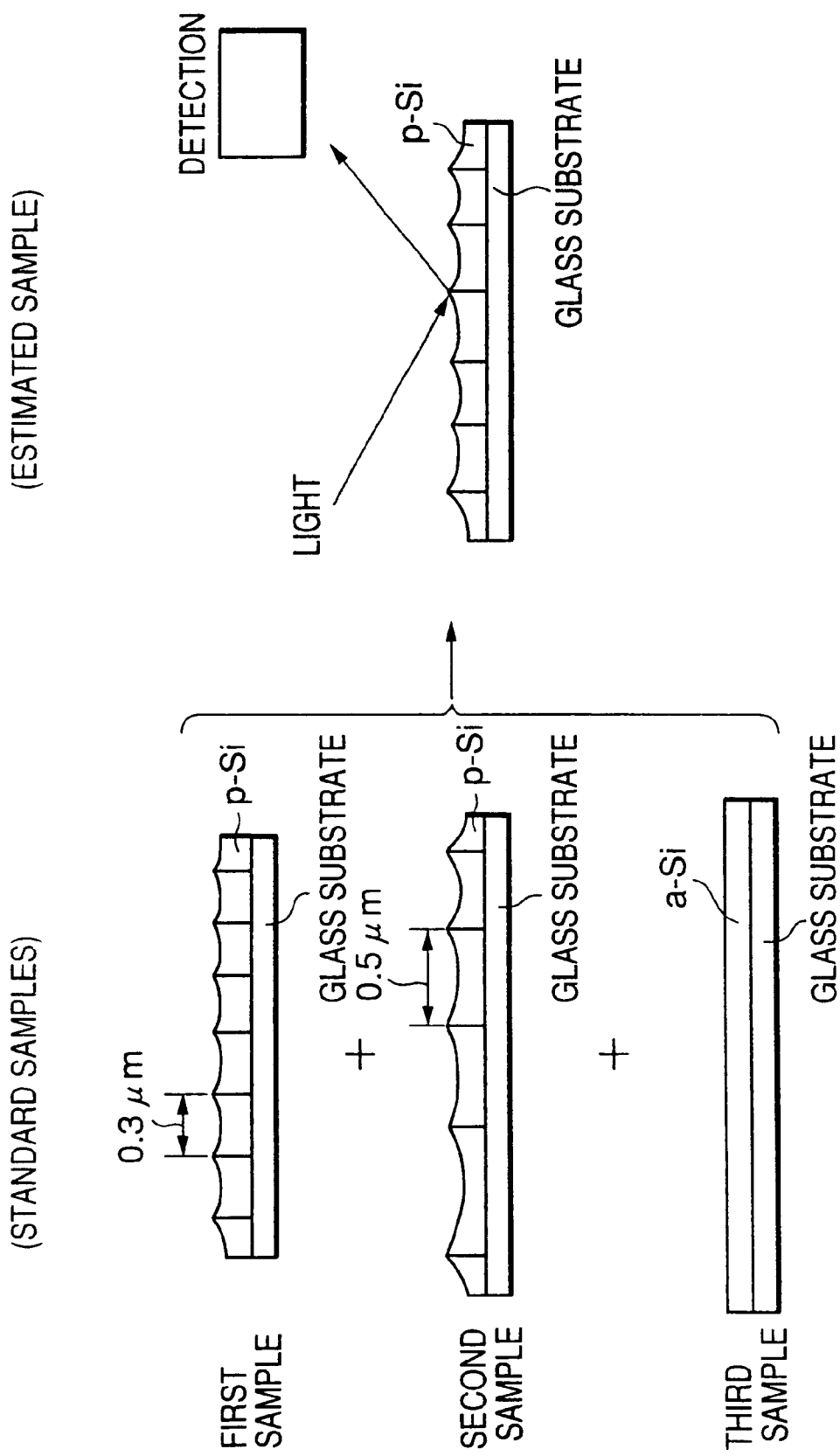
FIG. 4 is a sectional view showing the concept of the first preferred embodiment of a polycrystalline semiconductor film inspecting method according to the present invention.

First, referring to FIGS. 4 through 6, the first preferred embodiment of a polycrystalline semiconductor film inspecting method serving as a basic principle according to the present invention will be described below. In the first preferred embodiment of a polycrystalline semiconductor film inspecting method according to the present invention, first, second and third samples serving as standard samples are separately formed as shown in FIG. 4. While three types of samples, i.e., the first through samples, serving as standard samples have been formed in this preferred embodiment, only two types of polycrystalline semiconductor film samples, i.e., only the first and second samples, as the minimum number of samples may be formed to apply the present invention.

In the first preferred embodiment shown in FIG. 4, the first sample is a polycrystalline silicon film having a crystal grain size of 0.3 $\mu$m formed on a glass substrate. The second sample is a polycrystalline silicon film having a crystal grain size of 0.5 $\mu$m formed on a glass substrate, and the third sample is an amorphous silicon film formed on a glass substrate. These standard samples are previously prepared, and dependence on wavelength of a light refractive index of each of the standard samples and dependence on wavelength of a damping coefficient thereof are previously measured to calculate the values thereof.

Then, as shown on right side of FIG. 4, a polycrystalline silicon film serving as a sample to be estimated, which is an object to be inspected, is prepared, and the sample to be estimated is irradiated with light to measure a light refractive index and a light damping coefficient of the polycrystalline silicon film to calculate dependence on wavelength of the refractive index and dependence on wavelength of the damping coefficient.

Figure 5:
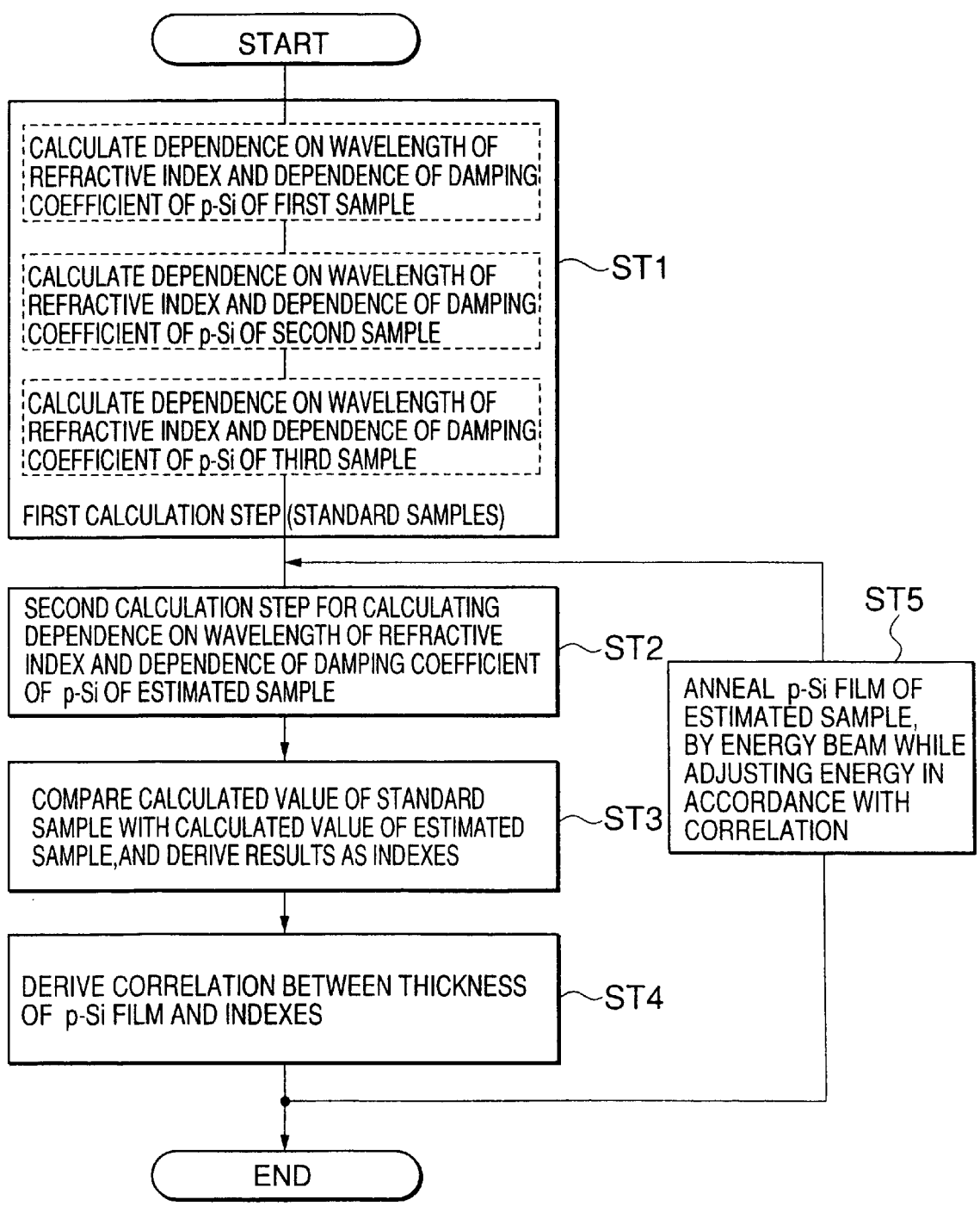
FIG. 5 is a flow chart showing steps of the first preferred embodiment of a polycrystalline semiconductor film inspecting method according to the present invention.
Figure 6:
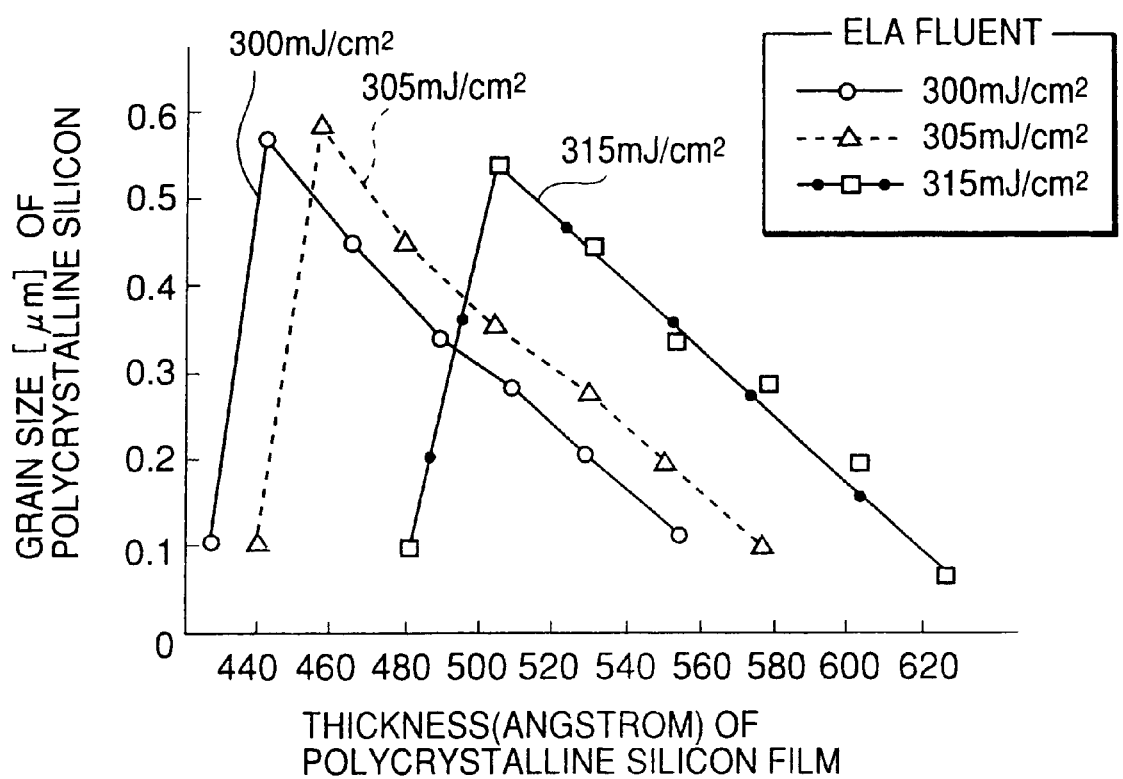
FIG. 6 is a graph showing the relationship between thickness of a polycrystalline silicon film and silicon crystal grain sizes in the first preferred embodiment.

Referring to FIG. 5, processing steps of the first preferred embodiment of a polycrystalline semiconductor film inspecting method according to the present invention will be described. First, at step ST1, dependence on wavelength of a refractive index and dependence on wavelength of a damping coefficient for each of the first through third polycrystalline silicon film samples serving as the standard samples are calculated. Then, at a second calculating step ST2, dependence on wavelength of a refractive index, dependence on wavelength of a damping coefficient, and a thickness of a polycrystalline semiconductor film serving as an object to be estimated are calculated. Then, at a comparison step ST3, the dependencies on wavelength of the refractive index and damping coefficient for the polycrystalline semiconductor film serving as the object to be estimated are compared with those for the polycrystalline semiconductor films serving as the standard samples, and the results thereof are obtained as indexes. Then, a correlation step ST4, the correlation between the thickness of the polycrystalline semiconductor film and the indexes obtained at the comparison step is derived. Finally, in accordance with the correlation obtained at the correlation step SP4, anneal is carried out while adjusting energy of an energy beam irradiated on the polycrystalline silicon film serving as the sample to be estimated.

Thus, in view of the previously obtained dependencies on wavelength of the refractive index and damping coefficient of the standard samples, the dependence on wavelength of the polycrystalline silicon film is measured, and a beam is implanted while adjusting the dose of energy while it is compared with the values obtained using the standard samples, so that it is possible to obtain a desired polycrystalline silicon film. The relationship between the crystal grain sizes of polycrystalline silicon and the thickness of the silicon film in that case is shown in FIG. 6. As can be seen from this graph, there is a certain correlation between the thickness of the polycrystalline silicon film and the crystal grain size, so that it is possible to obtain a desired polycrystalline film by adjusting the crystal grain size in accordance with the thickness of the film.

The second preferred embodiment of a polycrystalline semiconductor film inspecting method according to the present invention will be described below.

Figure 7:
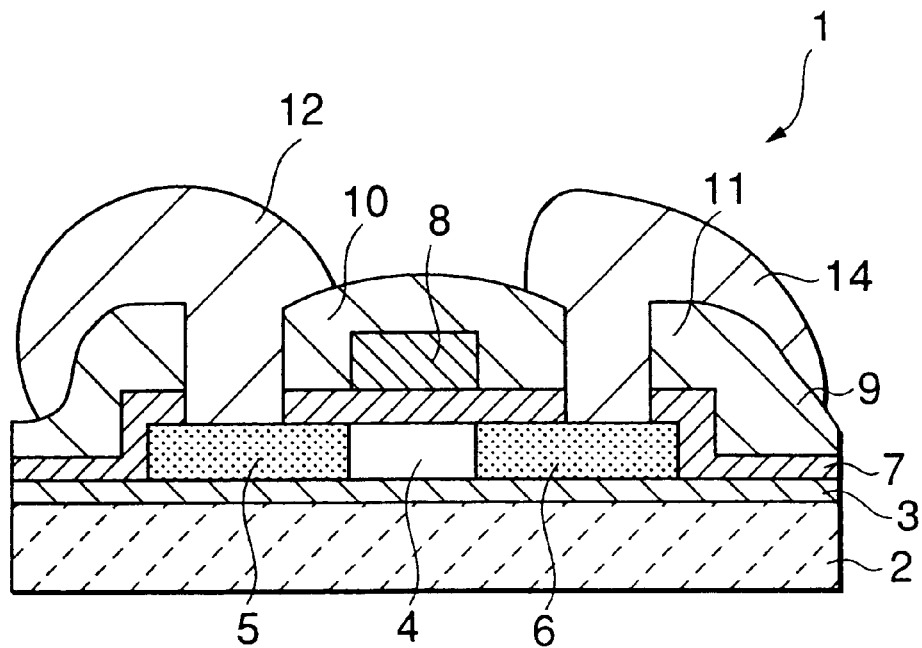
FIG. 7 is a sectional view of an embodiment of a thin film transistor.

First, referring to FIG. 7, a thin film transistor used for, e.g., 12-inch class drive circuit integrated liquid crystal display, will be described. As shown in FIG. 7, a buffer layer 3 having a laminated structure of a silicon nitride (SiNx) and silicon oxide (SiOx) is formed on an insulating substrate 2. On the buffer layer 3, there are formed a channel 4 of a polycrystalline silicon wherein a peak value of a refractive index (n) at 2.95~3.55 eV is limited to 6.28 or less, e.g., of a polycrystalline silicon serving as a polycrystalline semiconductor having a mean grain size of 0.24 $\mu$m~0.45 $\mu$m, and a drain region 5 and a source region 6 which are formed by impurity implantation.

Moreover, a gate insulator film 7 is formed on the buffer layer 3 including the channel 4, the drain region 5 and the source region 6. A gate electrode 8 is formed on the gate insulator film 7 above the channel 4. An interlayer insulator film 9 is formed on the gate electrode 8. The interlayer insulator film 9 has contact holes 10 and 11, which are filled with a drain electrode 12 and a source electrode 14, respectively, which are connected to the drain region 5 and the source region 6, respectively.

Furthermore, in order for the 12-inch drive class circuit integrated liquid crystal display to achieve a good display, the mean grain size of the polycrystalline silicon must be in the range of from 0.24 $\mu$m to 0.45 $\mu$m, so that the peak value appeared at 3.25±0.30 eV in the polycrystalline silicon formed by the excimer laser anneal (ELA) must be set to be less than 6.28 eV.

While the thin film transistor shown in FIG. 7 has been described as an example of an coplanar type transistor, the present invention should not be limited thereto, but the invention may be applied to a stagger type or reverse stagger type thin film transistor.

Figure 8:
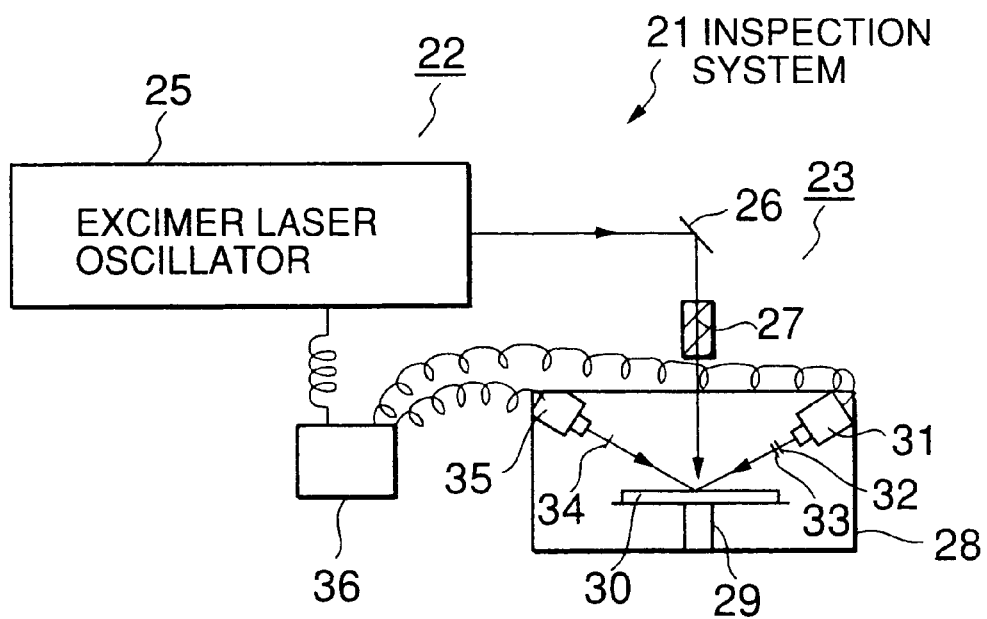
FIG. 8 is a conceptual drawing of a preferred embodiment of a polycrystalline silicon film inspecting system according to the present invention.

Referring to FIG. 8, the second preferred embodiment of a system for inspecting a thin film transistor of a polycrystalline silicon, according to the present invention, will be described below. In FIG. 8, a polycrystalline silicon thin film inspection system 21 comprises an XeCl excimer laser anneal system 22, and a spectral ellipsometer system 23 integral therewith.

The excimer laser anneal system 22 has an excimer laser oscillator 25 having a variable fluent which is one of forming conditions. After a laser beam from the excimer laser oscillator 25 reflects on an optical mirror 26, the waveform of the laser beam is adjusted by a beam homogenizer 27, and the waveform adjusted laser beam is supplied to a casing 28 of the spectral ellipsometer system 23. The casing 28 houses therein: a position adjustable, movable table 29 for mounting thereon a sample 30; a light source 31 for irradiating on the sample 30 with a light; a chopper 32; polarizers 33 and 34; and a rotating analyzer 35. The amorphous silicon sample 30 mounted on the table 29 is also irradiated with the light which has reflected on the optical mirror 26.

The spectral ellipsometer system 23 has the light source 31 for irradiating the sample 30 with light. The sample 30 is irradiated with the light from the light source 31 via the chopper 32 and the polarizer 33. Then, the light reflects on the sample 30 to be incident on the rotating analyzer 35. Since the light source 31 and the rotating analyzer 35 are connected to a personal computer 36, the outgoing light from the light source 31 and the light received by the rotating analyzer 35 are analyzed by means of the personal computer 36. The results are fed back to the excimer laser oscillator 25.

At this time, if the grain size of the sample 30 is too large, the fluent of the laser beam from the excimer laser oscillator 25 is reduced, and if the grain size of the sample 30 is too small, the fluent of the laser beam is increased. The feedback of the fluent may be carried out in a sheet of the sample 30. In this case, the fluent may be changed while annealing the sample 30. Alternatively, the thickness of an amorphous silicon film may be measured immediately before the excimer laser anneal, to be used as one of setting information on the fluent of the excimer laser oscillator 25.

Figure 9:
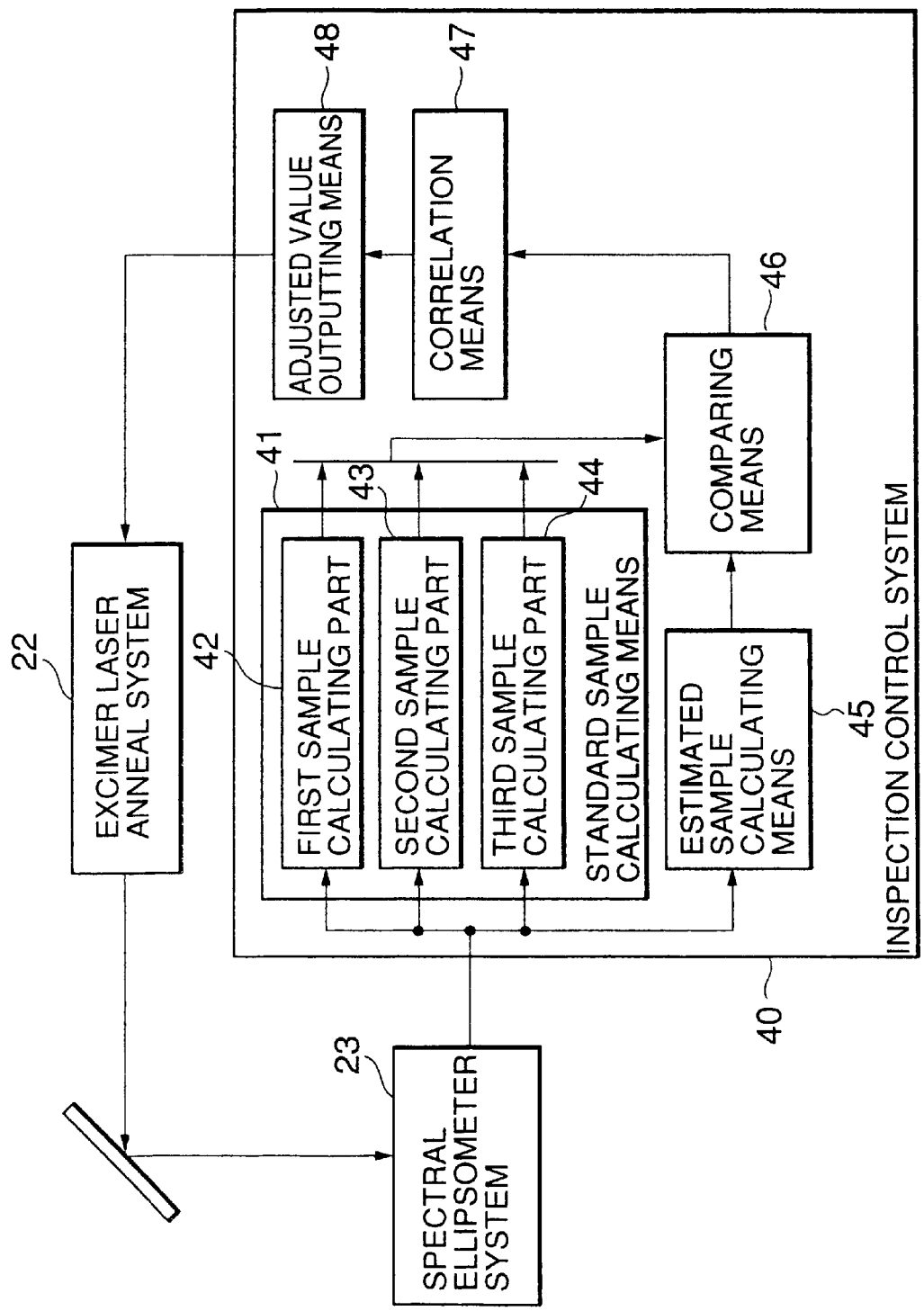
FIG. 9 is a block diagram of the second preferred embodiment of a polycrystalline semiconductor film inspecting system according to the present invention.

FIG. 9 shows the more detailed construction of the second preferred embodiment of a polycrystalline silicon film inspecting system according to the present invention. As shown in FIG. 9, the polycrystalline silicon film inspecting system comprises an excimer laser oscillator system 22, a spectral ellipsometer system 23 and inspection control system 40. The inspection control system 40 comprises standard sample calculating means 41, estimated sample calculating means 45, comparing means 46 for comparing the values calculated by the calculating means 41 and 45, correlation means 47 for deriving a correlation between both samples on the basis of the output of the comparing means 46, and adjusted value outputting means 48 for adjusting the quantity of a laser beam, which is oscillated by the excimer laser oscillator system 22, on the basis of the output of the correlation means 47. Furthermore, also in the second preferred embodiment similar to the first preferred embodiment, the standard sample calculating means 41 has first through third sample calculating parts 42 through 44, and is designed to previously calculate dependence on wavelength of a refractive index and dependence on wavelength of a damping coefficient for the first through third samples as shown in FIG. 4.

An inspection method using the polycrystalline silicon thin film inspecting system 21 shown in FIG. 8 will be described below. For example, the sample 30 is a polycrystalline silicon film having a laminated structure of a silicon nitride (SiNx) film having a thickness of 50 nm, a silicon oxide (SiOx) film having a thickness of about 100 nm and an amorphous silicon film of about 55 nm, which is formed on a glass substrate by the excimer laser anneal method using a XeCl excimer laser. For example, laser beams having irradiation energies of about 341 mJ/cm$^2$ and 305 mJ/cm$^2$ are irradiated 26 times, respectively. In addition, it is assumed that the mean grain sizes of the polycrystalline silicon film are about 0.52 $\mu$m and about 0.31 $\mu$m, and the surface irregularities are about 22 nm and about 53 nm, respectively.

In addition, a sample having a laminated structure of a silicon nitride (SiNx) film having a thickness of about 50 nm, a silicon oxide (SiOx) film having a thickness of about 100 nm and an amorphous silicon having a thickness of about 55 nm on the glass substrate is prepared as a standard sample.

Then, the polarization characteristics of these standard samples are measured by means of a spectral ellipsometer. Then, the polarization characteristics are analyzed to calculate dependencies on wavelength of refractive indexes (n) and damping coefficients (k) of the amorphous and polycrystalline silicon samples. The dependencies on wavelength of refractive indexes (n) of the obtained standard samples are represented by functions, $n_{a-Si}(\lambda)$ and $n6(\lambda)$.

Then, the polarization characteristics of the polycrystalline silicon sample, the grain size of which is to be measured, i.e., the polycrystalline silicon sample comprising a silicon nitride film having a thickness of about 50 nm, a silicon oxide film having a thickness of about 100 nm and a polycrystalline silicon film having a thickness of about 55 nm, which have been laminated on the glass substrate, and which serves as a sample to be inspected, are measured by a spectral ellipsometer.

Figure 10:
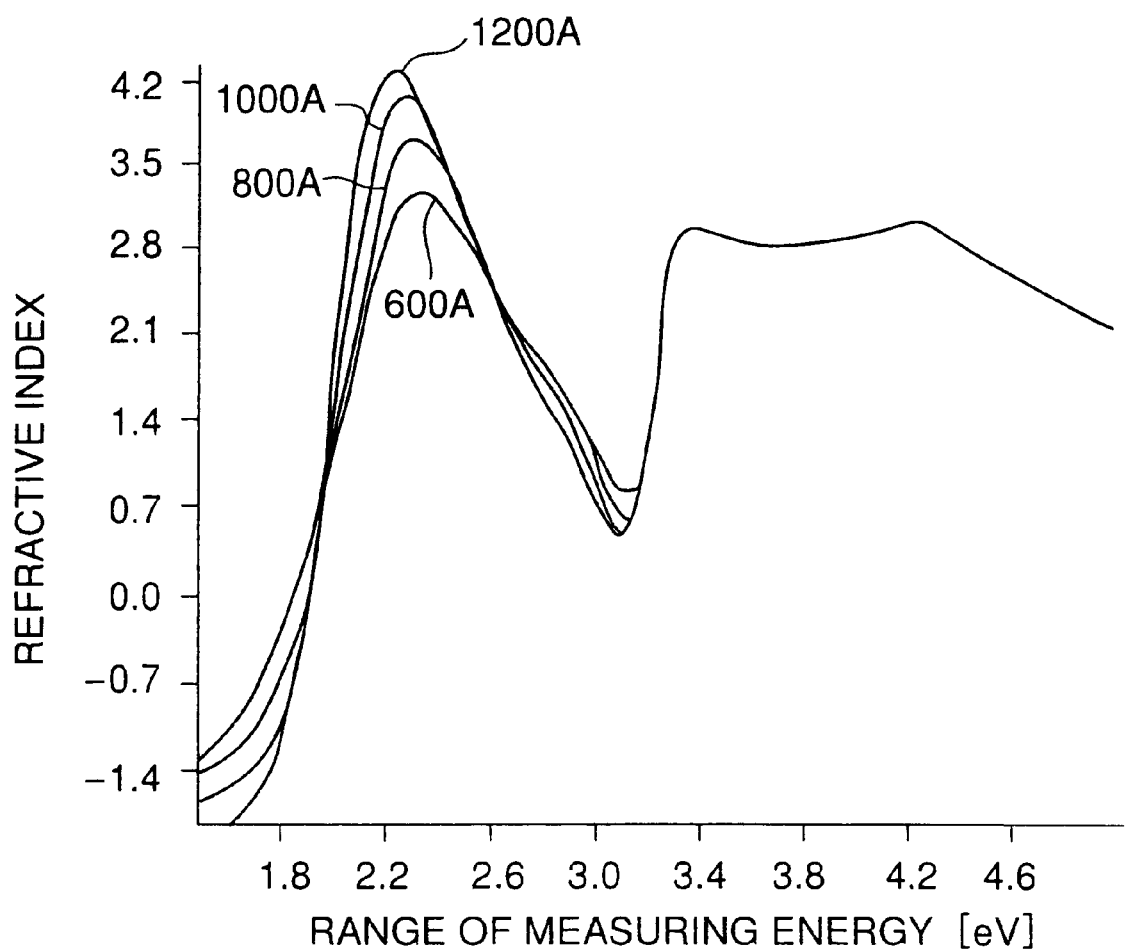
FIG. 10 is a graph showing the relationship between dependence on wavelength of a refractive index of a laminated structure of a glass substrate, a silicon nitride film, a silicon oxide film and a polycrystalline silicon film, and measuring energy to a silicon oxide film.
Figure 11:
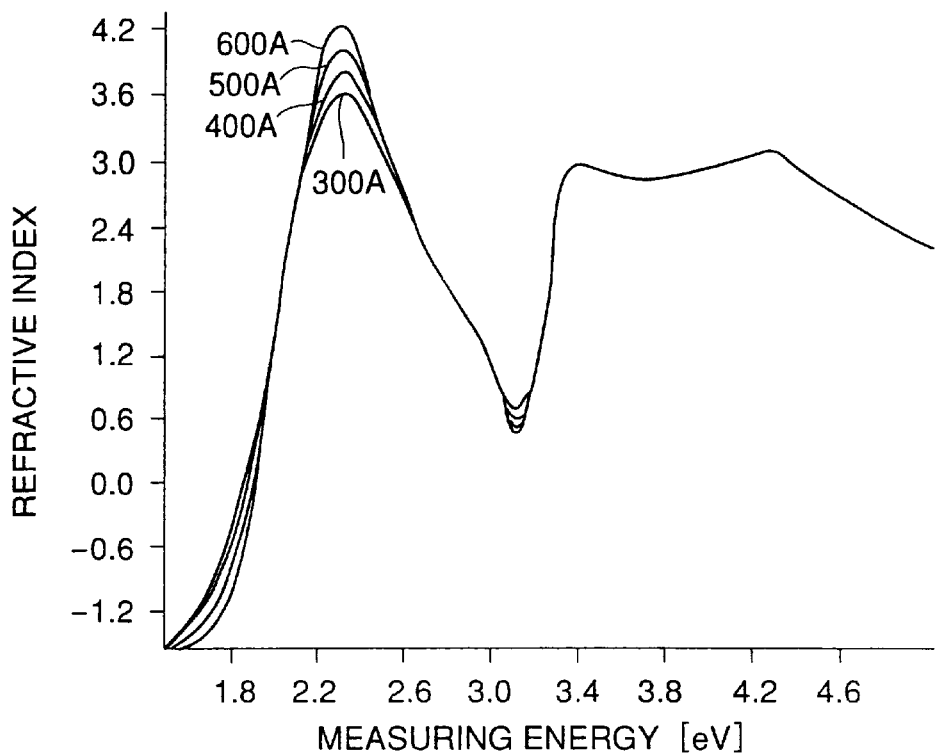
FIG. 11 is a graph showing the relationship between dependence on wavelength of a refractive index of a laminated structure of a glass substrate, a silicon nitride film, a silicon oxide film and a polycrystalline silicon film, and dependence on thickness of a silicon nitride film.

In this measurement, the measuring energy is preferably in the range of from 2.0 eV to 5.0 eV. Because the range of measuring energy has an influence on variations in thickness of the silicon oxide and silicon nitride films underlying the polycrystalline silicon film in the range of from 1.5 eV to 2.0 eV as shown in FIGS. 10 and 11 although most of commercially available typical systems can measure in the range of from 1.5 eV to 2.0 eV.

It is assumed that dependencies on wavelength of reflective indexes and damping coefficients, which have been calculated by the polarization characteristics, are represented by functions $k(\lambda)$ and $n(\lambda)$, respectively. These functions $k(\lambda)$ and $n(\lambda)$ are represented by the functions $n_{a-Si}(\lambda)$, $n5(\lambda)$, $n6(\lambda)$, $k_{a-Si}(\lambda)$, $k5(\lambda)$ and $k6(\lambda)$, and g, h and i simultaneously satisfying the following formulae are determined.

$$k(\lambda)=g*k5(\lambda)+h*k6(\lambda)+i*k_{a-Si}(\lambda)$$

$$n(\lambda)=g*n5(\lambda)+h*n6(\lambda)+i*n_{a-Si}(\lambda)$$

$$g+h+i=1$$

Figure 12:
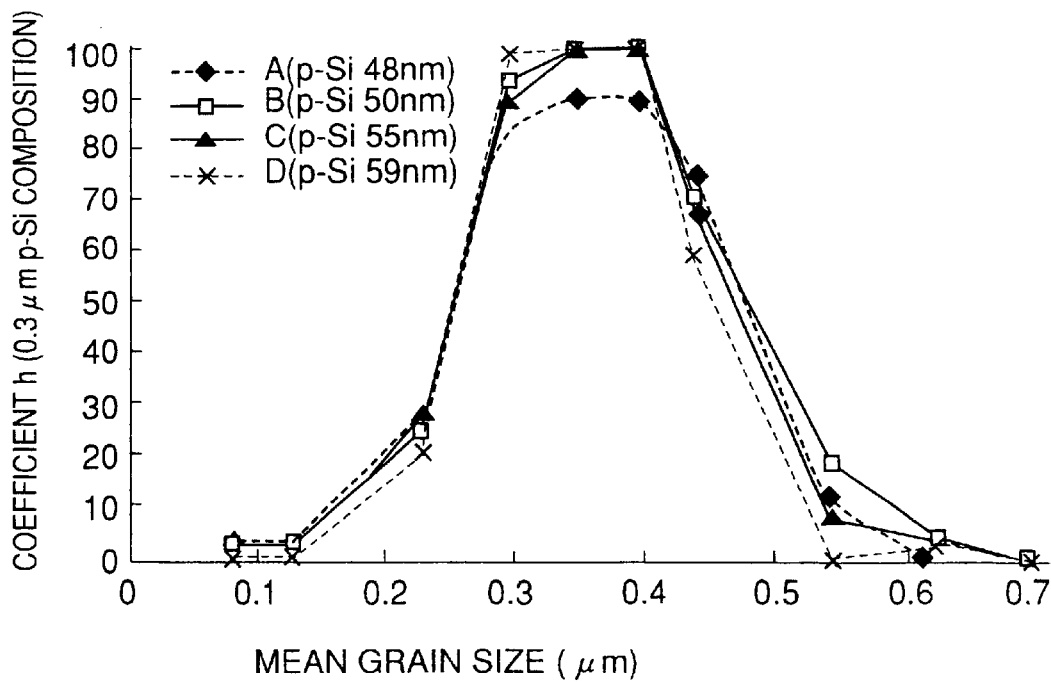
FIG. 12 is a graph showing the relationship between proportions of compositions of a polycrystalline silicon (p-Si) film having a thickness of 0.3 $\mu$m and mean grain sizes of the polycrystalline silicon film when the polycrystalline silicon film is represented by a polycrystalline silicon film having a thickness of 0.3 $\mu$m and a polycrystalline silicon film having a thickness of 0.5 $\mu$m.

FIG. 12 shows the relationship between coefficients and grain sizes in the optical characteristics of h, i.e., the polycrystalline silicon film having a thickness of 0.3 µm. It can be seen from FIG. 12 that if the value of h is greater than or equal to 0.3, the mean grain size is in the range of from 0.25 µm to 0.45 µm.

Figure 13:
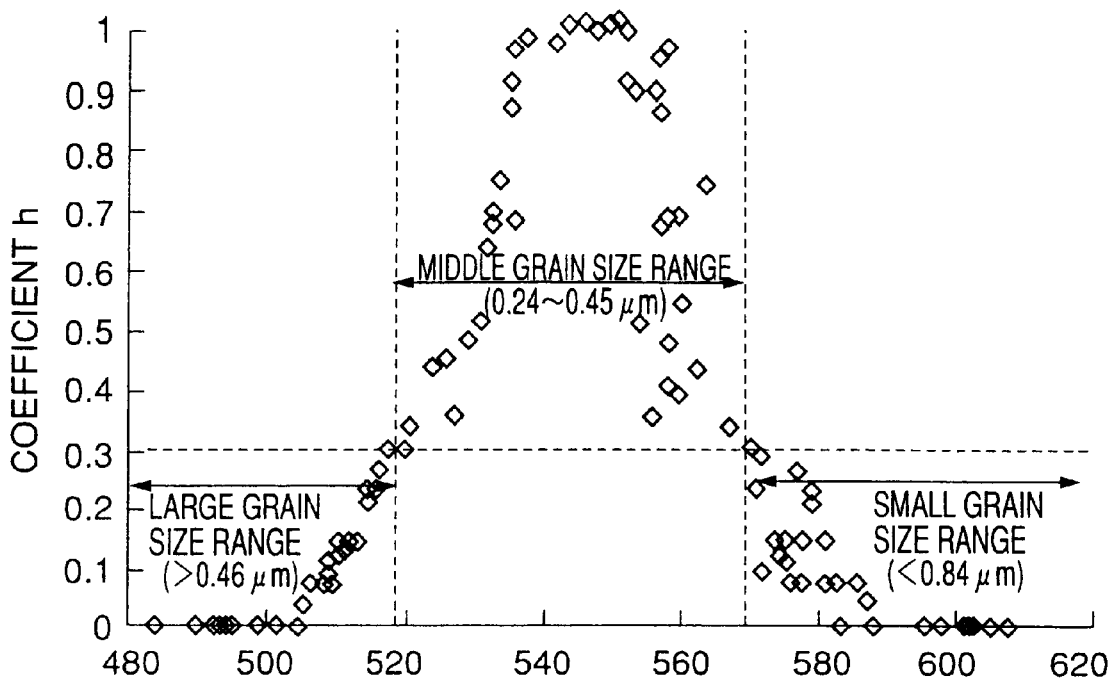
FIG. 13 is a graph showing the relationship between proportions of compositions of a polycrystalline silicon film having a mean grain size of 0.3 $\mu$m and film pressures of the polycrystalline silicon film.

Moreover, as shown in a correlation diagram of FIG. 13, the grain size is a medium grain size ranging from 0.25 µm to 0.45 µm when h≧0.3, a large grain size of 0.46 µm or more when h<0.3 and the polycrystalline silicon film is thin, or a small grain size of 0.249 µm or less when h<0.3 and the polycrystalline silicon film is thick. Furthermore, the reason why the value of h is different even if the thickness of the polycrystalline silicon film is the same is that the output of fluent of the excimer laser anneal varies in the range of ±7%. In addition, a polycrystalline silicon having a large grain size is suitable for a thin film transistor since the mobility of crystals thereof is reasonably high. Thus, it is possible to accurately distinguish non-defective from defective in a short time.

While the functions $k_{a-Si}(\lambda)$ and $n_{a-Si}(\lambda)$ indicative of dependencies on wavelength of the refractive index and damping coefficient of the amorphous silicon film have been used as the third functions representing $k(\lambda)$ and $n(\lambda)$ of the polycrystalline silicon film, the present invention should not be limited thereto. According to the present invention, it is possible to sufficiently inspect the polycrystalline silicon film using other functions in place of the above functions. Moreover, even if fourth functions and fifth functions are used, the effects of classification of the mean grain sizes into three ranges of 0.24 µm or less, from 0.25 to 0.45 µm, and 0.46 µm or more are the same. Furthermore, this method can also calculate the margin of thickness of the silicon film produced by the excimer laser anneal.

Another preferred embodiment of a method and system for inspecting a polycrystalline semiconductor film, according to the present invention, will be described below. This preferred embodiment uses Ψ and Δ which represent a ratio of a reflectance of an s-polarized light to that of a p-polarized light by tan(Ψ)·exp(iΔ). Assuming that reflection coefficients of the s-polarized light and the p-polarized light are Rs and Rp, respectively, the values of Ψ and Δ are expressed by the following formula.

$$Rs/Rp=\tan(\Psi)\cdot\exp(i\Delta)$$

A method for inspecting, e.g., a polycrystalline silicon film having a laminated structure of a silicon nitride film of a thickness of about 50 nm, a silicon nitride film having a thickness of about 100 nm and a polycrystalline silicon film having a thickness of about 55 µm on a glass substrate, will be described below. Furthermore, the polycrystalline silicon film is formed by the excimer laser anneal.

First, two standard samples of a polycrystalline silicon and an amorphous silicon, which have different means grain sizes and surface irregularities, are prepared. Preferably, these standard samples have the same structure as that of the sample to be inspected. This preferred embodiment also uses a polycrystalline silicon film, which has a laminated structure of a silicon nitride film having a thickness of about 50 nm, a silicon oxide film having a thickness of about 100 nm and an amorphous silicon film having a thickness of about 55 nm and which is formed on a glass substrate by the excimer laser anneal method using a XeCl excimer laser.

In this preferred embodiment, laser beams having irradiation energies of about 342 mJ/cm² and about 305 mJ/cm² are irradiated 26 times, respectively, and it is assumed that the polycrystalline silicon films have mean grain sizes of about 0.52 µm and about 0.31 µm, and the surface irregularities are about 22 nm and about 53 nm, respectively. In addition, a sample having a laminated structure of a silicon nitride film having a thickness of about 50 nm, a silicon oxide film having a thickness of about 100 nm and an amorphous silicon film having a thickness of about 55 nm on a glass substrate is prepared.

Then, the polarization characteristics of these standard samples are measured by means of a spectral ellipsometer. Then, the polarization characteristics are analyzed to calculate Ψ and Δ of the amorphous silicon film and the respective polycrystalline silicon films. The dependencies on wavelength of Ψ of the obtained standard samples are expressed by functions $\Psi_{a-Si}(\lambda)$, $\Psi5(\lambda)$ and $\Psi6(\lambda)$, and the dependencies on wavelength of Δ thereof are expressed by functions $\Delta_{a-Si}(\lambda)$, $\Delta5(\Psi)$ and $\Delta6(\Psi)$.

Then, the polarization characteristics of the polycrystalline silicon sample, the grain size of which is to be measured, i.e., the sample to be inspected, which has a laminated structure of the silicon nitride film of about 50 nm, the silicon oxide film of about 100 nm and the polycrystalline silicon film of about 55 nm on the glass substrate, are measured by means of a spectral ellipsometer. It is assumed that the dependencies on wavelength of Ψ and Δ calculated from the polarization characteristics are represented by functions $\Psi(\lambda)$ and $\Delta(\lambda)$, respectively. These functions $\Psi(\lambda)$ and $\Delta(\lambda)$ are represented by the functions $\Psi_{a-Si}(\lambda)$, $\Psi6(\lambda)$, $\Delta_{a-Si}(\lambda)$, $\Delta5(\lambda)$ and $\Delta6(\lambda)$, and g, h and i simultaneously satisfying the following formulae are determined.

$$\Psi(\lambda)=g*\Psi5(\lambda)+h*\Psi6(\lambda)+i*\Psi_{a-Si}(\lambda)$$

$$\Delta(\lambda)=g*\Delta5(\lambda)+h*\Delta6(\lambda)+i*\Delta_{a-Si}(\lambda)$$

$$g+h+i=1$$

Figure 14:
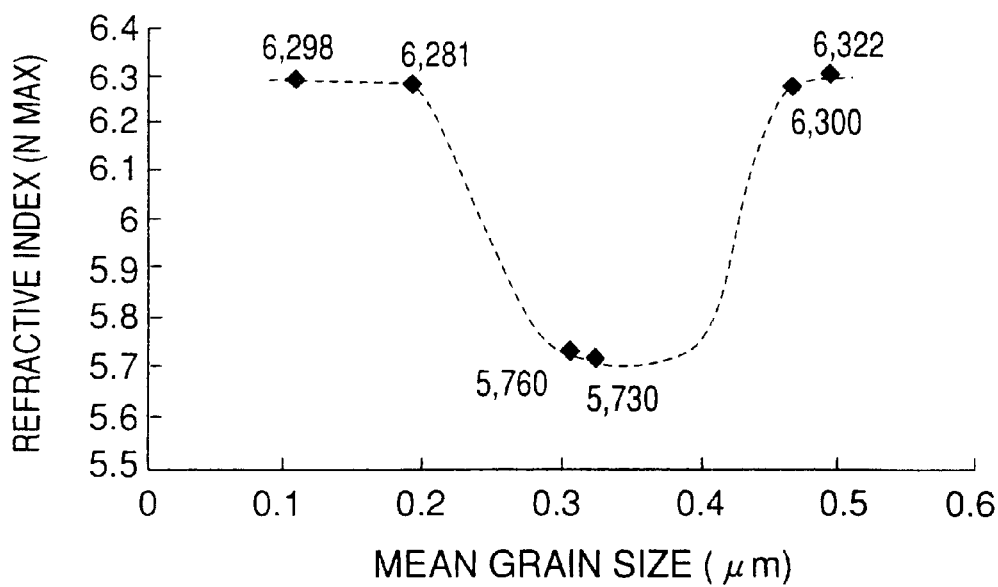
FIG. 14 is a graph showing the relationship between dependence of a grain size and the maximum refractive index of polycrystalline silicon films having mean grain sizes of 0.1 $\mu$m, 0.3 $\mu$m and 0.5 $\mu$m.

Also in this preferred embodiment using different functions, similar to the correlation diagram of FIGS. 13 and 14, the grain size is a medium grain size ranging from 0.25 µm to 0.45 µm when h≧0.3, a large grain size of 0.46 µm or more when h<0.3 and the polycrystalline silicon film is thin, or a small grain size of 0.24 µm or less when h<0.3 and the polycrystalline silicon film is thick.

The mean grain sizes of the standard samples should not be limited to those in the above preferred embodiment, but the mean grain sizes may be 0.4 µm and 0.6 µm, or 0.3 µm and 0.7 µm. Thus, although any combinations of mean grain sizes may be optionally selected, at lease one standard sample preferably has a refractive index, a damping coefficient, Ψ or Δ in the range of a mean grain size of from 0.2 µm to 0.5 µm. Because the surface morphology in the case of a mean grain size of from 0.2 µm to 0.5 µm is worse than those in the case of other mean grain size ranges to increase the surface roughness, so that the factors of surface roughness are treated as variations in refractive index, damping factor and coefficients Ψ and Δ. Moreover, the mean grain sizes may be divided into three ranges of, e.g., 0.4 µm or less, from 0.5 µm to 0.6 µm, and 0.7 µm or more.

Moreover, if an object may be inspected using the thickness of an amorphous silicon film, which has been measured before the excimer laser anneal, in place of the thickness of a polycrystalline silicon film.

Since the mean grain size is preferably in the range of from 0.25 µm to 0.45 µm when a 12-inch class drive circuit integrated LCD is produced, the polycrystalline silicon film used for the thin film transistor shown in FIG. 7 preferably has a peak value of refractive index, which is 6.28 or less appeared at 3.35 eV±0.30 eV, in accordance with FIG. 14.

Moreover, in any preferred embodiments of a method for inspecting a polycrystalline silicon film according to the present invention, it is possible to accurately measure a mean grain size in short time of, e.g., 5 seconds, in a non-destructive, non-contact manner. In particular, in a liquid crystal display of a low density thin film transistor of a polycrystalline silicon, it is possible to accurately select a polycrystalline silicon having a mean grain size of 0.46 μm. Therefore, if the present invention is applied to quality control for the steps of producing a polycrystalline silicon, it is possible to improve tact time to reduce manufacturing costs.

As described in detail above, in accordance with a method and system for inspecting a polycrystalline semiconductor film according to the present invention, it is possible to quantify the optically measured results by measuring a standard sample and a sample to be estimated, which serves as an object to be inspected, so that it is possible to accurately measure a crystal grain size in a short time in a non-destructive, non-contact manner.

Moreover, if a polycrystalline semiconductor film to be estimated is annealed while adjusting energy in accordance with a derived correlation between the measured results of a standard sample and a sample to be estimated, the mean crystal grain size contained in the polycrystalline semiconductor film can be set to be a desired size.

Referring to the accompanying drawings, the third preferred embodiment of a polycrystalline semiconductor film inspecting method and system according to the present invention will be described in detail below. Also in this preferred embodiment similar to the first preferred embodiment, while a silicon film is used as a semiconductor film, the present invention should not be limited thereto, but the invention may be applied to other semiconductor films. For example, the present invention may be applied to semiconductor films of germanium (Ge), gallium arsenide (GaAs), cadmium selenide (CdSe) and so forth.

A polycrystalline silicon film, which serves as an object to be inspected by the third preferred embodiment of a polycrystalline silicon film inspecting method according to the present invention, comprises three layers, e.g., a silicon nitride (SiNx) having a thickness of about 50 nm deposited on a glass substrate, a silicon oxide (SiOx) layer having a thickness of about 100 nm deposited thereon, and a polycrystalline silicon (p-Si) layer having a thickness of about 55 nm. The polycrystalline silicon layer is formed by the excimer laser anneal (ELA) method.

Then, standard samples are prepared. In this case, two types of polycrystalline film samples having different mean grain sizes and surface irregularities, and an amorphous silicon (a-Si) film are prepared. It is desired that these standard samples have the same structure as that of a sample to be inspected, which is an object to be inspected.

In the case of the third preferred embodiment of a polycrystalline film inspecting method, the polycrystalline silicon film serving as the standard sample is a polycrystalline silicon (p-Si) film having a structure of, e.g., a silicon nitride (SiNx) layer having a thickness of about 50 nm, a silicon oxide (SiOx) layer having a thickness of about 100 nm, and an amorphous silicon (a-Si) layer having a thickness of about 55 nm, which are deposited on a glass substrate by the ELA method using an XeCl laser. In this ELA method, laser beams having irradiation energies of about 341 mJ/cm$^2$ and 305 mJ/cm$^2$ are irradiated, e.g., 26 times, respectively, to prepare p-Si samples having mean grain sizes of about 0.52 μm and about 0.31 μm and surface irregularities of about 22 m and about 53 μm, respectively.

Figure 15:
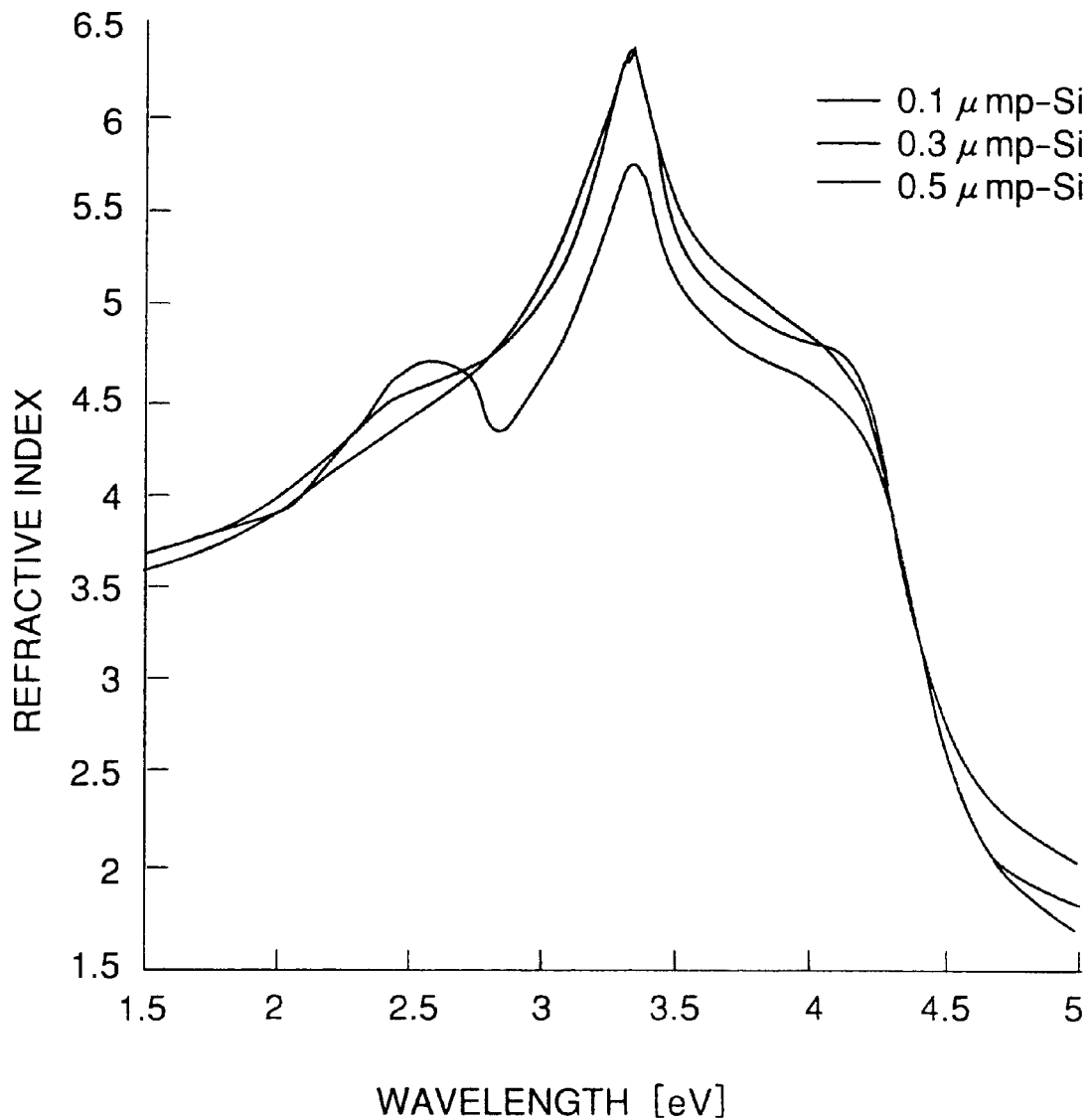
FIG. 15 is a graph showing dependence on wavelength of a refractive index in the third preferred embodiment of a polycrystalline semiconductor film inspecting method according to the present invention.

Then, the standard samples are set in a spectral ellipsometer to measure the polarization characteristics thereof. In this case, the measuring energy may be in the range of from about 1.5 to 5.0 eV. The polarization characteristics of the standard samples are analyzed to calculate dependencies on wavelength of dielectric constants (∈), refractive indexes (n) and damping coefficients (k) of the polycrystalline silicon samples. As a result, the obtained dielectric constants (∈), refractive indexes (n) and damping coefficients (k) of the respective polycrystalline silicon samples can be represented by functions of wavelength. For example, in the case of the dependencies on wavelength derived from the refractive indexes (n) and damping coefficient (k), n5(λ) and n6(λ), and k5(λ) and k6(λ) are defined as functions of the respective dependencies on wavelength. As an example thereof, dependence on wavelength of a refractive index is shown in FIG. 15.

The polarization characteristics of the polycrystalline silicon sample, the grain size of which is to be measured and wherein the SiNx film having a thickness of about 50 nm, the SiOx film having a thickness of about 100 nm and the polycrystalline silicon film having a thickness of about 55 nm are deposited on the glass substrate, are measured by the spectral ellipsometer. Assuming that the projecting portion of the polycrystalline silicon (p-Si) calculated on the basis of the measured polarization characteristics and the layer of a natural oxide film comprise one layer and assuming that dependencies on wavelength of reflective indexes and damping coefficients thereof are represented by functions k(λ) and n(λ), respectively, which are represented by the functions n5(λ), n6(λ), $n_{siox}(\lambda)$, k5(λ), k6(λ) and $k_{siox}(\lambda)$ of the standard sample, g, h and i simultaneously meeting the following formulae are determined.

$$k(\lambda)=g*k5(\lambda)+h*k6(\lambda)+i*k_{siox}(\lambda)$$

$$n(\lambda)=g*n5(\lambda)+h*n6(\lambda)+i*n_{siox}(\lambda)$$

$$g+h+i=1$$

In this case, it is assumed that the used model has a structure wherein a natural oxide film is simply deposited on a polycrystalline silicon (p-Si) layer.

Figure 16:
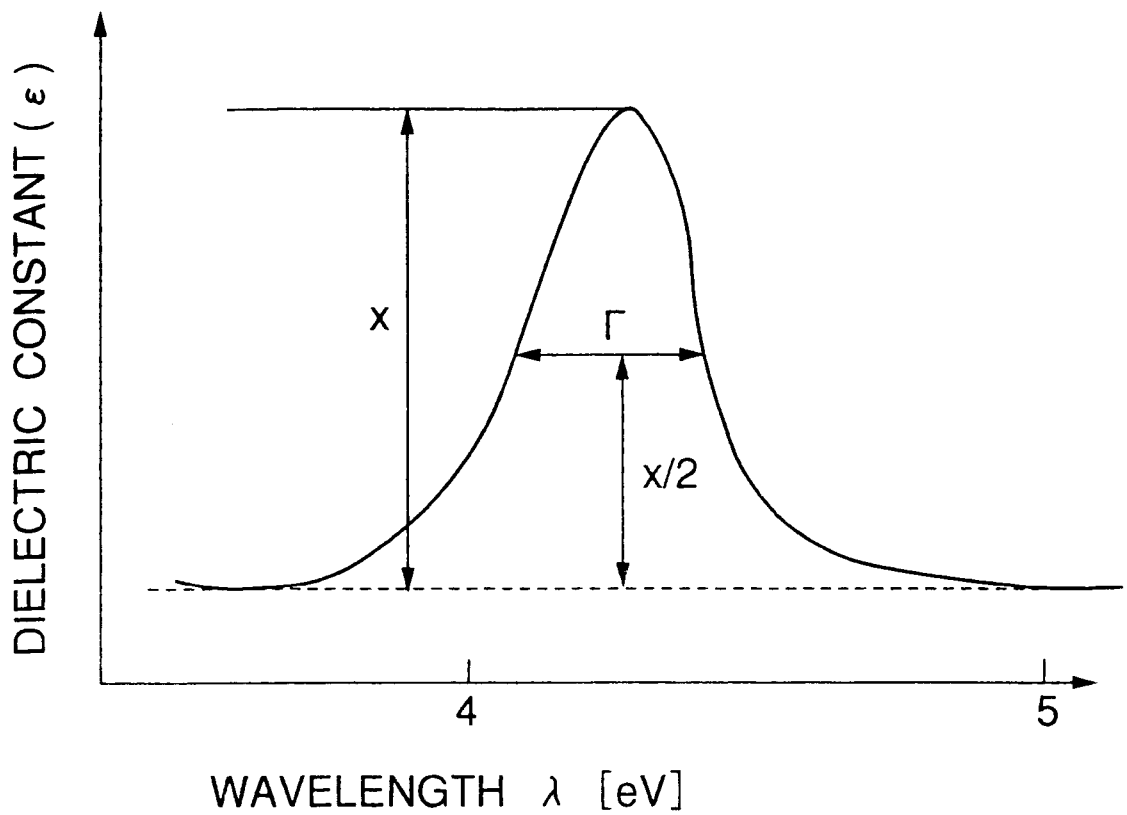
FIG. 16 is a graph showing dependence on wavelength of a dielectric constant (∈) of a polycrystalline silicon in the third preferred embodiment of a polycrystalline semiconductor film inspecting method according to the present invention.
Figure 17:
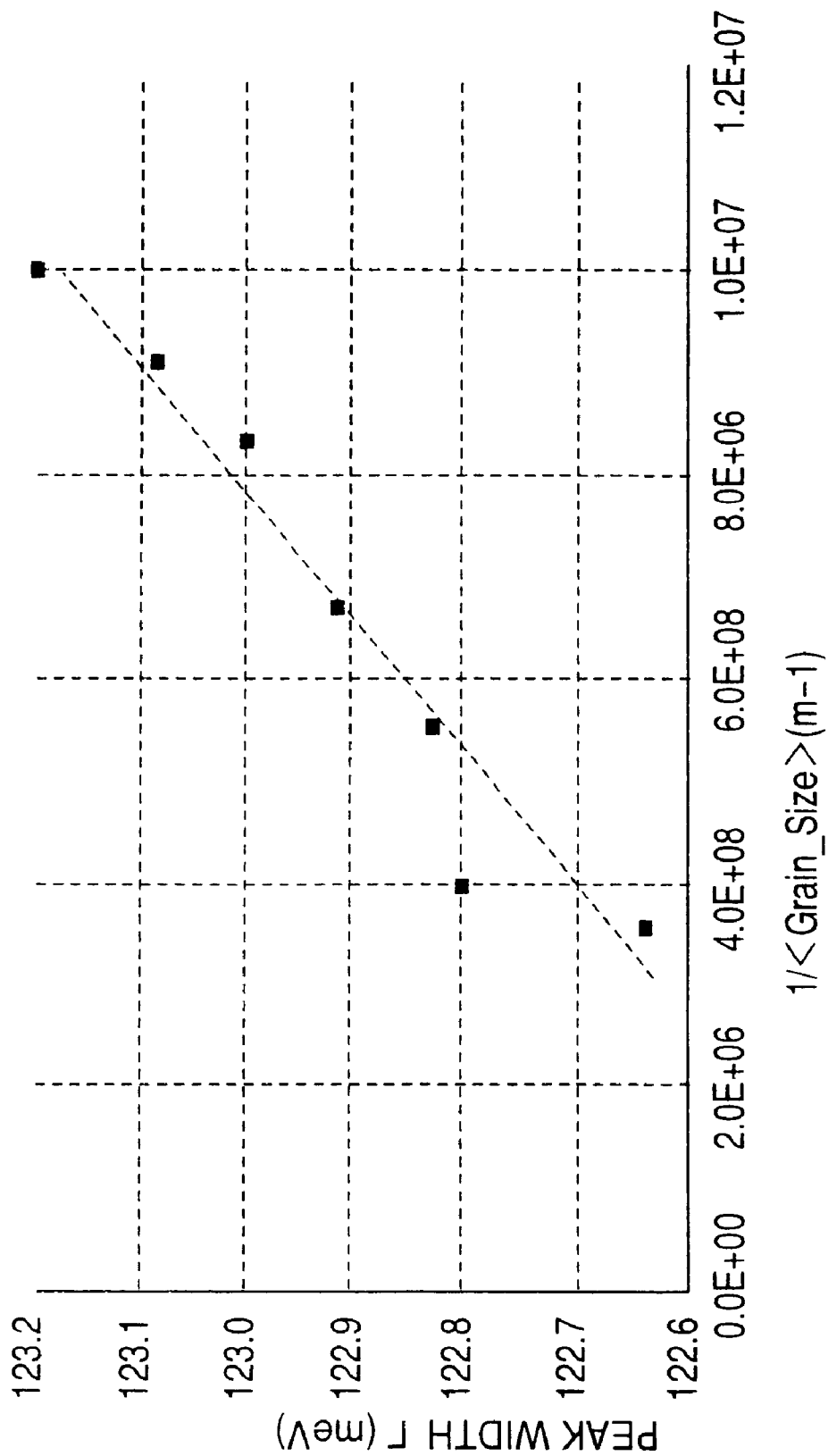
FIG. 17 is a graph showing the relationship between mean grain sizes of polycrystalline silicon and peak widths at half height in the third preferred embodiment.

Moreover, with respect to a polycrystalline silicon (p-Si) layer capable of assuming that the surface thereof is flat, a function of dependence on wavelength of a dielectric constant is calculated. At this time, as shown in FIG. 16, the peak width (Γ) at half height of the polycrystalline silicon (p-Si) near 4 eV is calculated. If the correlation between Γ on ordinate and mean grain sizes on abscissa is plotted, a correlation diagram of FIG. 17 can be obtained. On the basis of the calibration curve appeared in this correlation diagram, the grain size can be calculated from Γ of the measured sample.

The feature of the present invention is that the projection on the surface of a polycrystalline silicon (p-Si) film and a layer of a natural oxide film are used as a mixed layer so that the polarization characteristics of the polycrystalline silicon (p-Si) film can be treated as those in a polycrystalline silicon (p-Si) film having a flat surface, and that it is assumed that the compositions thereof include a polycrystalline silicon (p-Si) having grain sizes of 0.3 μm and 0.5 μm other than oxide films. Thus, it is possible to suitably represent surface irregularities, so that it is possible to detect optical compositions of a polycrystalline silicon (p-Si) film, having a flat portion.

Furthermore, although the present invention can be particularly applied to the accurate measurement of crystals of a polycrystalline silicon having a grain size of 0.05 to 0.35 μm or less, the invention may be applied to the measurement of grain sizes of any polycrystalline silicon having other ranges of grain size.

In the production of LCD arrays for liquid crystal displays, it is very important that it is possible to accurately measure crystals having a grain size of 0.05 to 0.35 μm or less, since the LCD can not be operated well unless the grain size of the crystal is 0.25 μm or more. The present invention has been made in view of this point, the present invention can be changed and modified in various ways as long as it is possible to accurately measure a crystal having a grain size of 0.05 to 0.35 μm.

In the above described first through third preferred embodiments, while the polycrystalline semiconductor film inspecting method has used examples of two formulae as functional formulae for deriving dependencies on wavelength of the refractive index and damping coefficient thereof, the present invention should not be limited thereto, but the following functional formulae may be used. That is, when k(λ) and n(λ) are represented by functions n3(λ), n4(λ), k3(λ) and k4(λ) of the standard sample, d and e simultaneously meeting the following formulae may be determined to derive dependencies on wavelength.

$$k(\lambda)=d*k3(\lambda)+e*k4(\lambda)$$

$$n(\lambda)=d*n3(\lambda)+e*n4(\lambda)$$

$$d+e=1$$

What is claimed is:

1. A polycrystalline semiconductor film inspecting method for measuring grain sizes of semiconductor grains contained in a polycrystalline semiconductor film, the method comprising:

a first calculation step of calculating dependencies on wavelength of a refractive index and a damping coefficient of a plurality of standard samples including at least a polycrystalline semiconductor film;

a second calculation step of calculating dependencies on wavelength of a refractive index and a damping coefficient, and a thickness of an estimated sample consisting of a polycrystalline semiconductor film as an object to be inspected;

a comparison step of comparing said dependencies on wavelength of the refractive index and the damping coefficient of said estimated samples with those of said standard samples, to derive the compared results as indexes; and a correlation step of deriving a correlation between said thickness of said estimated example and said indexes derived at said comparison step.

2. A polycrystalline semiconductor film inspecting method as set forth in claim 1, which further comprises an energy beam annealing step of annealing said estimated sample, while adjusting energy in accordance with said correlation derived at said correlation step.

3. A polycrystalline semiconductor film inspecting method as set forth in claim 1, wherein said comparison step compares said dependencies on wavelength of the refractive index and the damping coefficient between said estimated sample, and said plurality of standard samples including at least one of an amorphous semiconductor and a crystalline semiconductor.

4. A polycrystalline semiconductor film inspecting method as set forth in claim 3, which further comprises an energy beam annealing step of annealing said estimated sample as the object to be inspected, while adjusting energy in accordance with said correlation derived at said correlation step.

5. A polycrystalline semiconductor film inspecting method for measuring grain sizes of semiconductor grains contained in a polycrystalline semiconductor film, the method comprising:

a first calculation step of calculating a ratio of a reflectance of a p-polarized light to that of an s-polarized light of a plurality of standard samples including at least a polycrystalline semiconductor film;

a second calculation step of calculating a ratio of a reflectance of a p-polarized light to that of an s-polarized light, and a thickness of an estimated sample consisting of a polycrystalline semiconductor film as an object to be inspected;

a comparison step of comparing the ratio of the reflectance of said estimated sample with the ratio of the reflectance of said standard samples, to derive the compared results as indexes; and a correlation step of deriving a correlation between said thickness of said estimated example and said indexes derived at said comparison step.

6. A polycrystalline semiconductor film inspecting method as set forth in claim 5, which further comprises an energy beam annealing step of annealing said estimated sample as the object to be inspected, while adjusting energy in accordance with said correlation derived at said correlation step.

7. A polycrystalline semiconductor film inspecting system comprising the steps of:

forming a plurality of standard samples including at least a polycrystalline semiconductor film having different mean grain sizes by an energy beam anneal method;

calculating dependence on wavelength of a dielectric constant of each of said plurality of standard samples by means of a spectral ellipsometer;

forming an estimated sample consisting of a polycrystalline semiconductor film, which serves as an object to be inspected, by the energy beam anneal method;

calculating dependence on wavelength of dielectric constant of said estimated sample as the object to be inspected, and calculating the thickness thereof;

comparing said dependence on wavelength of the dielectric constant of said estimated sample with those of said standard samples; and deriving a correlation to a peak width at half height of said dielectric constant calculated at said comparing step.

8. A polycrystalline semiconductor film inspecting method as set forth in claim 7, wherein said estimated sample consisting of the polycrystalline semiconductor film has a mean crystal grain size of substantially 0.3 μm.

9. A polycrystalline semiconductor film inspecting method as set forth in claim 8, wherein the polycrystalline semiconductor film included in said standard samples has a mean crystal grain size of substantially 0.5 μm.

10. A polycrystalline semiconductor film inspecting method comprising the steps of:

irradiating a polycrystalline semiconductor film, which is formed on a substrate, with a light, and detecting dependence on wavelength of the intensity of a reflected light; and comparing said dependence on wavelength of the intensity of the reflected light with a sample data, and calculating a crystal grain size of said polycrystalline semiconductor film or data correlate therewith.

11. A polycrystalline semiconductor film inspecting system for measuring grain sizes of semiconductor grains contained in a polycrystalline semiconductor film, the system comprising:

measuring means for measuring dependencies on wavelength of a refractive index and a damping coefficient of a plurality of standard samples including at least a polycrystalline semiconductor film, and for measuring dependencies on wavelength of a refractive index and a damping coefficient, and a thickness, of an estimated sample consisting of a polycrystalline semiconductor film serving as an object to be inspected;

comparing means for comparing said dependencies on wavelength of the refractive indexes and the damping coefficients of said estimated sample with those of said plurality of standard samples, and for comparing the thickness of said estimated sample with that of said standard samples, to derive the compared results as indexes; and correlation means for deriving a correlation between said thickness of said estimated sample and said indexes calculated by said comparing means.

12. A polycrystalline semiconductor film inspecting system as set forth in claim 11, which further comprises energy beam annealing means for annealing said estimated sample as the object to be inspected, while adjusting energy in accordance with said correlation derived by said correlation means.

13. A polycrystalline semiconductor film inspecting system as set forth in claim 11, wherein said comparing means compares said dependencies on wavelength of the refractive index and the damping coefficient between said estimated sample as the object to be inspected, and at least one of an amorphous semiconductor and a crystalline semiconductor included in said standard samples.

14. A polycrystalline semiconductor film inspecting system as set forth in claim 13, which further comprises energy beam annealing means for annealing said estimated sample serving as the object to be inspected, while adjusting energy in accordance with said correlation derived by said correlation means.

15. A polycrystalline semiconductor film inspecting system for measuring grain sizes of semiconductor grains contained in a polycrystalline semiconductor film, the system comprising:

measuring means for measuring a ratio of a reflectance of a p-polarized light and that of an s-polarized light of a plurality of standard samples including at least a polycrystalline semiconductor film, and for measuring a ratio of a reflectance of a p-polarized light and that of an s-polarized light, and a thickness, of an estimated sample consisting of a polycrystalline semiconductor film serving as an object to be inspected;

comparing means for comparing said ratio of the reflectance of said estimated sample with the ratio of the reflectance of standard samples; and correlation means for deriving a correlation between said thickness of said estimated sample and said indexes calculated by said comparing means.

16. A polycrystalline semiconductor film inspecting system as set forth in claim 15, which further comprises energy beam annealing means for annealing said estimated sample serving as the object to be inspected, while adjusting energy in accordance with said correlation derived by said correlation means.

* * * * *